US010653738B2

(12) United States Patent
DeMeo

(10) Patent No.: US 10,653,738 B2
(45) Date of Patent: May 19, 2020

(54) TOPICAL MEDICATIONS FOR BRUISES AND BURNS

(71) Applicant: Meridian Research and Development, Inc., Coral Gables, FL (US)

(72) Inventor: Ronald F. DeMeo, Coral Gables, FL (US)

(73) Assignee: Meridian Research and Development Inc., Coral Gables, FL (US)

( * ) Notice: Subject to any disclaimer, the term of this patent is extended or adjusted under 35 U.S.C. 154(b) by 0 days.

(21) Appl. No.: 14/338,274

(22) Filed: Jul. 22, 2014

(65) Prior Publication Data

US 2016/0022676 A1    Jan. 28, 2016

(51) Int. Cl.

| A61K 31/505 | (2006.01) |
| A61K 31/137 | (2006.01) |
| A61K 31/167 | (2006.01) |
| A61K 31/138 | (2006.01) |
| A61K 9/00 | (2006.01) |
| A61K 36/28 | (2006.01) |
| A61K 45/06 | (2006.01) |
| A61P 17/02 | (2006.01) |
| A61K 31/122 | (2006.01) |
| A61K 31/135 | (2006.01) |
| A61K 31/07 | (2006.01) |
| A61K 33/38 | (2006.01) |
| A61K 31/4164 | (2006.01) |
| A61K 31/4402 | (2006.01) |
| A61K 31/00 | (2006.01) |
| A61K 31/635 | (2006.01) |

(52) U.S. Cl.
CPC ............ *A61K 36/28* (2013.01); *A61K 9/0014* (2013.01); *A61K 31/00* (2013.01); *A61K 31/07* (2013.01); *A61K 31/122* (2013.01); *A61K 31/135* (2013.01); *A61K 31/137* (2013.01); *A61K 31/138* (2013.01); *A61K 31/167* (2013.01); *A61K 31/4164* (2013.01); *A61K 31/4402* (2013.01); *A61K 31/505* (2013.01); *A61K 31/635* (2013.01); *A61K 33/38* (2013.01); *A61K 45/06* (2013.01); *A61P 17/02* (2018.01)

(58) Field of Classification Search
None
See application file for complete search history.

(56) References Cited

U.S. PATENT DOCUMENTS

| 3,792,161 | A | * | 2/1974 | Fox ...................... | A61K 9/0014 |
| | | | | | 424/94.67 |
| 4,748,022 | A | * | 5/1988 | Busciglio ............. | A61K 36/886 |
| | | | | | 424/539 |
| 4,985,459 | A | | 1/1991 | Sunshine et al. | |
| 5,496,812 | A | | 3/1996 | Platt | |
| 5,989,535 | A | * | 11/1999 | Nayak .................. | A61K 9/0031 |
| | | | | | 424/430 |
| 6,093,414 | A | * | 7/2000 | Capelli .................. | A01N 59/16 |
| | | | | | 424/405 |
| 6,433,061 | B1 | | 8/2002 | Marchant et al. | |
| 7,572,776 | B2 | | 8/2009 | Yu et al. | |
| 7,883,487 | B2 | | 2/2011 | Shantha et al. | |
| 2003/0175328 | A1 | | 9/2003 | Shefer et al. | |
| 2007/0128142 | A1 | * | 6/2007 | Harrison .................. | A61K 8/06 |
| | | | | | 424/70.12 |
| 2007/0259029 | A1 | | 11/2007 | McEntire et al. | |
| 2007/0275093 | A1 | | 11/2007 | Pierard et al. | |
| 2008/0311167 | A1 | * | 12/2008 | Oronsky ............... | A61K 9/0014 |
| | | | | | 424/402 |
| 2008/0317690 | A1 | * | 12/2008 | Battaglia ............... | A61K 9/0014 |
| | | | | | 424/60 |
| 2012/0141610 | A1 | * | 6/2012 | Gowey ................. | A61K 31/519 |
| | | | | | 424/725 |
| 2012/0149748 | A1 | | 6/2012 | Shanler et al. | |
| 2013/0337031 | A1 | | 12/2013 | Kisak et al. | |

* cited by examiner

*Primary Examiner* — Susan T Tran
*Assistant Examiner* — William Craigo
(74) *Attorney, Agent, or Firm* — Sideman & Bancroft LLP; Guy W. Chambers

(57) ABSTRACT

Topical medications to treat the physical effects of bruises and burns. For bruises, the topical medication preferably includes therapeutically effective amounts of vasoconstrictor, such as phenylephrine HCL USP, an anti-inflammatory, such as Arica, and compounding agents. In one embodiment, the compounding agents are a Versabase® gel which includes water, ammonium acryloyldimethyltaurate copolymer, aloe barbadensis leaf juice powder, allatoin, disodium EDTA, methylchloroisothiazolinone and methylisothiazolinone. For burns, the topical medication preferably combines therapeutically effective amounts of an active anti-bacterial compound, such as silver sulfadiazine, an anesthetic, such as lidocaine, and a histamine blocker, such as diphenhydramine, with suitable compounding agents, such as Versabase® gel. Both the anti-bruise and anti-burn medications of the present invention can advantageously be formulated in solutions, lotions, creams, ointments, gels, foams or transdermal patches.

1 Claim, 6 Drawing Sheets

TOPICAL MEDICATIONS FOR BRUISES AND BURNS

FIELD OF THE INVENTION

The present invention relates to topical medications for treating bruises and burns. More particularly, a topical medication which includes a vasoconstrictor and an anti-inflammatory agent has been found to dramatically reduce the swelling associated with bruises. A second topical medication which includes an anti-bacterial or anti-microbial compound, an anesthetic and a histamine blocker has been found to be effective in treating burns.

BACKGROUND OF THE INVENTION

A bruise (layman's term), also called a contusion (medical term), is a type of hematoma of tissue in which capillaries, and sometimes venules, are damaged by trauma, allowing blood to seep, hemorrhage or extravasate into the surrounding interstitial tissues. Trauma sufficient to cause bruising can occur from a wide variety of situations including accidents, falls and surgeries.

In a bruise, distress to tissue causes capillaries to break under the skin, allowing blood to escape and build up. As time progresses, blood seeps into the surrounding tissues, causing the bruise to darken and spread. Nerve endings within the affected tissue detect the increased pressure which, depending upon the severity and location, may be perceived as pain or pressure. The damaged capillary endothelium releases endothelin, a hormone that causes narrowing of the blood vessel to minimize bleeding. As the endothelium is destroyed, the underlying von Willebrand factor is exposed and initiates coagulation, which creates a temporary clot to plug the wound and eventually leads to restoration of normal tissue.

Treatment for light bruises is minimal and may include rest, ice, compression, elevation, painkillers and, later in recovery, light stretching exercises. Immediate application of ice while elevating the bruised area may help reduce swelling. Applying a medicated cream containing mucopolysccharide polysulfuric acid (e.g., Hirudoid) may speed the healing process. Other topical creams containing skin-fortifying ingredients, such as retinol or alpha hydroxy acids, can improve the appearance of bruising faster than if the bruise is left to heal on its own. Anti-inflammatory treatments in the *Arnica* family have also been used to treat bruises, with questionable efficacy.

A burn is a type of injury to skin caused by heat, electricity, chemicals, friction, lasers, ice or radiation. Burns that affect only the superficial skin are known as superficial or first-degree burns. When damage penetrates into some of the underlying layers, it is a partial-thickness or second-degree burn. In a full-thickness or third-degree burn, the injury extends to all layers of the skin. A fourth-degree burn involves injury to deeper tissues, such as muscle or bone.

The techniques used to treat burns depends upon the severity of the burn. Superficial burns may be managed with little more than simple pain relievers, while major burns may require prolonged treatment in specialized burn centers. Cooling with tap water or ice may help relieve pain and decrease damage. However, prolonged exposure to cold water or ice may also cause dermal injury, such as frost bite, and necrosis. Patients who use ice therapy for chronic pain can develop cold panniculitis or "ice-pack dermatitis" in which erythematous plaques occur. Further, ice is difficult to apply and should only be applied for short periods of time. In the case of extensive burn, the dermal barrier and thermal insulating properties of the skin is compromised and prolonged ice exposure can also lower body temperature to the point of hypothermia. Partial-thickness burns may require cleaning with soap and water, followed by dressings. Full-thickness burns usually require surgical treatments, such as skin grafting. Extensive burns often require large amounts of intravenous fluids because the subsequent inflammatory response will result in significant capillary fluid leakage and edema. The most common complications of burns are related to infection, pain and scaring.

While treatments have been developed to treat bruises and burns, they have varying degrees of effectiveness. In the case of bruises from facial injections and facial surgery, for example, the dark puffiness associated with the bruise can not only be painful, but also very embarrassing. There are anecdotal reports that *Arnica* taken before surgery can help reduce bruising but has little effect on the bruise once the bruise has occurred. For that reason, more effective treatments are needed to quickly minimize the effects of bruises and burns.

SUMMARY OF THE INVENTION

The present invention provides topical medications which significantly reduce the physical effects of bruises and burns. For bruises, the topical medication preferably combines therapeutically effective amounts of a vasoconstrictor, such as phenylephrine HCL USP, and an anti-inflammatory agent, such as Arica, with one or more compounding agents. In one embodiment, the compounding agents are a Versabase® gel which includes water, ammonium acryloyldimethyltaurate copolymer, aloe barbadensis leaf juice powder, allatoin, disodium EDTA, methylchloroisothiazolinone and methylisothiazolinone.

For burns or wounds, the topical medication of the present invention preferably combines therapeutically effective amounts of an anti-bacterial compound, such as silver sulfadiazine, an anesthetic, such as lidocaine, and a histamine blocker, such as diphenhydramine, with suitable compounding agents. As with the bruise medication, Versabase® gel may be used as a compounding agent for the anti-burn medication. Both the anti-bruise and anti-burn medications of the present invention can advantageously be formulated in solutions, lotions, creams, ointments, gels, foams or transdermal patches.

DETAILED DESCRIPTION OF THE PREFERRED EMBODIMENTS

Figure 1:
FIG. 1 shows the first day of a leg burn caused by hot coffee.

The topical medications of the present inventions may be formulated in solutions, lotions, creams, ointments, gels, foams or transdermal patches. Topical solutions are of low viscosity and often use water or alcohol as the base. Topical solutions are usually formed by dissolving powder in water, alcohol and sometimes oil. If alcohol is used as the base, it can cause drying of the skin. Lotions are similar to solutions but are thicker and tend to be more emollient in nature than solutions. Lotions usually have an oil mixed with water and, more often than not, have less alcohol than solutions.

A cream has an emulsion of oil and water in approximately equal proportions. It penetrates the stratum corneum outer layer of the skin well. Cream is thicker than lotion and maintains its shape when removed from its container. It tends to be moderate in moisturizing tendency.

An ointment is a homogeneous, semi-solid preparation, most commonly a greasy, thick oil (e.g., oil 80%-water 20%) with a high viscosity, that is intended for external application to the skin or mucus membranes. Ointments are formulated using hydrophobic, hydrophilic or water-emulsifying bases to provide preparations that are immiscible, miscible or emulsifiable with skin secretions. Ointments can also be derived from hydrocarbon (fatty), absorption, water-removable or water-soluble bases. Gels are often a semisolid emulsion, such as cellulose, in an alcohol or acetone base.

Transdermal patches can be a very precise time release method of delivering a drug. The release of the active component from a transdermal patch may be controlled by diffusion through the adhesive which covers the whole patch, by diffusion through a membrane which may only have adhesive on the patch rim or controlled by release from a polymer matrix.

To treat bruises, the topical medication of the present invention preferably combines therapeutically effective amounts of a vasoconstrictor and an anti-inflammatory agent with a compounding agent. When tissue is injured, the body produces both vasodilator and inflammatory agents that lead to edema and bruising. Since both mechanisms are in place, neither the vasoconstrictor nor anti-inflammatory alone would be ideal to prevent or treat active bruising. By combining a vasoconstrictor compound with an anti-inflammatory compound in the present invention, there is much more effective bruise and swelling prevention and treatment.

The vasoconstrictor of the present invention should be able to activate the alpha-adrenergic receptors found on the pre-capillary and post-capillary blood vessels. Activation of these receptors by either direct binding of the sympathomimetic agent to the binding site of the receptor or by the enhanced release of norepinephrine produces vasoconstriction. Such vasoconstriction decreases blood flow and thereby results in tissue shrinkage. The vasoconstrictor not only helps prevent and resolve a bruise, it can reduce and even stop active bleeding.

A preferred vasoconstrictor for the present invention is phenylephrine, which is sold commercially as Neosynephrine®. Alternative vasoconstrictors include epinephrine, oxymetazoline (commercially sold as Afrin®), pseudoephedrine, mephentermine, metaraminol, midodrine, norepinephrine, isoproterenol, dobutamine, dopamine, methylphenidate, mephedrone, tetrahydrozoline, brompheniramine, xylometazoline, chlorpheniramine, caffeine, antihistamines, other members of the adrenaline family and other alpha adrenergic receptor agonists. Phenylephrine is more preferred for the present invention compared to, for example, epinephrine because epinephrine, which acts on both alpha and beta adrenergic receptors, has significant cardiac risks. Phenylephrine, by comparison, is a selective to the alpha 1 receptor agonist and, therefore, has little cardiac risk. In the topical bruise medication of the present invention, the vasoconstrictor is preferably at a concentration between 0.1% and 10% by weight. In one gel embodiment, the vasoconstrictor is phenylephrine at a concentration of 0.5% by weight. 0.5% is a phenylephrine concentration which has received FDA approval for over-the-counter decongestant sales and, thus, should be acceptable to the FDA for over-the-counter topical medication sales for the present invention.

A preferred anti-inflammatory for the present invention is Arica, an *Arnica montana* L. botanical. *Arnica montana* L. (*arnica*) and *Artemisia absinthium* L. (wormwood) are two herbaceous perennial plants native to temperate regions of Europe. They belong to the same plant family, Asteraceae, and sub-family, Asteroideae, but *A. montana* is widely distributed in mountainous areas while *A. absinthium* naturally grows at the edge of fields or rocky slopes. While *arnica* has been known as an anti-inflammatory for topically treating skin bruises, contusions and pain, it has no known vasoconstriction properties. Besides *arnica* compounds, alternative anti-inflammatories that can be used in the present invention include Vitamin K (with or without retinol), non-steroidal anti-inflammatory drugs (NSAID), such as ibuprofen and aspirin cream, and steroidal creams, such as hydrocortisone. In the topical bruise medication of the present invention, the anti-inflammatory is preferably at a concentration between 0.1% and 20% by weight. In one gel embodiment, the anti-inflammatory is Arica at a concentration of 1.0% by weight.

Selection of suitable compounding agents will depend, to some extent, on whether the topical medication of the present invention is formulated in solutions, lotions, creams, ointments, gels, foams or transdermal patches. Topical solutions, for example, will have greater concentrations of water and/or alcohol than a topical ointment. In one preferred topical gel of the present invention for treating bruises, a phenylephrine HCL USP powder at a 0.5% concentration is combined with an *Arnica* flower tincture liquid at a 1.0% concentration and a Versabase® gel compounding agent. The Versabase® gel includes water, ammonium acryloyldimethyltaurate copolymer, aloe barbadensis leaf juice powder, allantoin, disodium EDTA, methylchloroisothiazolinone and methylisothiazolinone.

The topical bruise medication of the present invention is preferably applied to the skin either before or after the contusion. In the case of surgery, when the topical bruise medication was applied immediately before or after surgery, there was substantial prevention and reduction of bruising as well as substantial improvement in swelling. Although the principal intent of the bruise medication is to reduce and treat bruises, other unexpected effects of the bruise medication were the reduction in non-traumatic reddening (as in the condition known as Rosacea), the reduction in non-traumatic edema (such as swelling under the eyes), and skin tightening with line reduction.

A second topical medication of the present invention can reduce the detrimental effects of skin burns, particularly first and second degree skin burns. The topical burn medication of the present invention combines therapeutically effective amounts of an anti-bacterial or anti-microbial compound, such as silver sulfadiazine, a histamine blocker, such as diphenhydramine, and an anesthetic, such as lidocaine, with suitable compounding agents to form a solution, lotion, cream, ointment, gel, foam or transdermal patch.

In addition to silver sulfadiazine, other suitable anti-bacterial or anti-microbial ingredients include mafenide acetate, silver nitrate, sulfonamide, cetrimide, retapamulin, mafenide, mupirocin, neomycin, polymyxin B, erythromycin, polysporin, tetracycline or a combination of these. Among the variety of anti-bacterial and anti-microbial agents, silver compounds have long been recognized as having the advantage of a broad anti-microbial spectrum of activity against gram-negative and gram-positive bacteria with minimal development of bacterial resistance. In addition to being an anti-biotic, silver compounds are also anti-fungal, Other anti-fungal agents that can be used as an alternative to or in addition to silver compounds include ciclopirox, benzoic acid, flucytosine, griseofulvin, heloprogin, toinaftate, undecylenic acid, crystal violet, balsam of Peru, piroctone olamine, zinc pyrithione, selenium sulfide and tar.

A histamine blocker is a pharmaceutical that inhibits the action of histamine by either blocking its attachment to histamine receptors or inhibiting the enzymatic activity of histidine decarboxylase which catalyzes the transformation of histidine into histamine. Histamine not only causes pain and itching, it also produces edema. The pathogenesis of burn edema is that histamine and its metabolic derivatives increase the catalytic activity of xanthine oxidase. In addition to diphenhydramine, other suitable histamine blockers include doxylamine, astemizole, brompheniramine, chlorpheniramine, clemastine, loratadine, promethazine and cimetidine. Topical anti-histamines not only reduce itching, they can also enhance the barrier function of the skin.

As with the bruise medication of the present invention, Versabase® gel may be used as a compounding agent for the anti-burn medication. Aquaphor® is another compounding agent that can be used in the anti-burn medication. Aquaphor® and petroleum jelly are petroleum-based ointments that are commonly used to keep post-operative wounds moist. While they improve wound healing, they also may cause wound redness and swelling. The histamine blocker of the anti-burn medication of the present invention will alleviate such redness and swelling.

Burns can be very painful and pruritic. Although the histamine blocker will reduce the pruritus, it will not reduce pain. When a wound or dermatitis is painful, the patient will often rub the wound or dermatitis thereby causing further skin damage, infection and scar formation. The addition of a local anesthetic, such as lidocaine, will provide pain relief and reduce the self-contamination. Alternatives to lidocaine include prilocaine, benzocaine, pramoxine and tetracaine.

Using the burn cream of the present invention, a two-fold improvement in wound healing was observed when compared with the application of topical anti-biotic ointments instead. Moreover, an unexpected result was that the burn creams of the present invention were able to treat a number of skin disorders, such as atopic dermatitis. A dramatic improvement was observed in itching, skin appearance and barrier function. In the case of chronic dermatitis, the pathogenesis starts as an allergy or hypersensitivity to a fungus. This causes a histamine release with dermatitis and barrier disruption. By having both an anti-bacterial/anti-fungal compound and an anti-histamine, the burn cream of the present invention addresses both the fungus and histamine problems. The anti-burn cream of the present invention may provide relief to a variety of chronic inflammatory dermatologic conditions.

While the topical medications of the present invention have, up to this point, been described for treating separate conditions (i.e., bruises versus burns), the topical medications of the present invention can advantageously be used together in a successive regimen in certain circumstances. For example, vasoconstriction is important to stop the bleeding of an acute cut. For this purpose, it is advantageous to apply the topical anti-bruise cream of the present invention to an acute cut. Nonetheless, once the cut starts to heal, sometimes over a period of weeks, circulation is critical for new skin to form in a way that prevents scarring and infection. To promote such circulation, it is helpful to apply a vasodilator, such as the lidocaine used in the topical anti-burn cream of the present invention.

Example 1: Treatment of Coffee Burn with Anti-Burn Cream

Figure 2:
FIG. 2 shows the FIG. 1 leg burn six days after an anti-burn cream of the present invention was applied.
Figure 3:
FIG. 3 shows the FIG. 1 leg burn thirteen days after an anti-burn cream of the present invention was applied.
Figure 4:
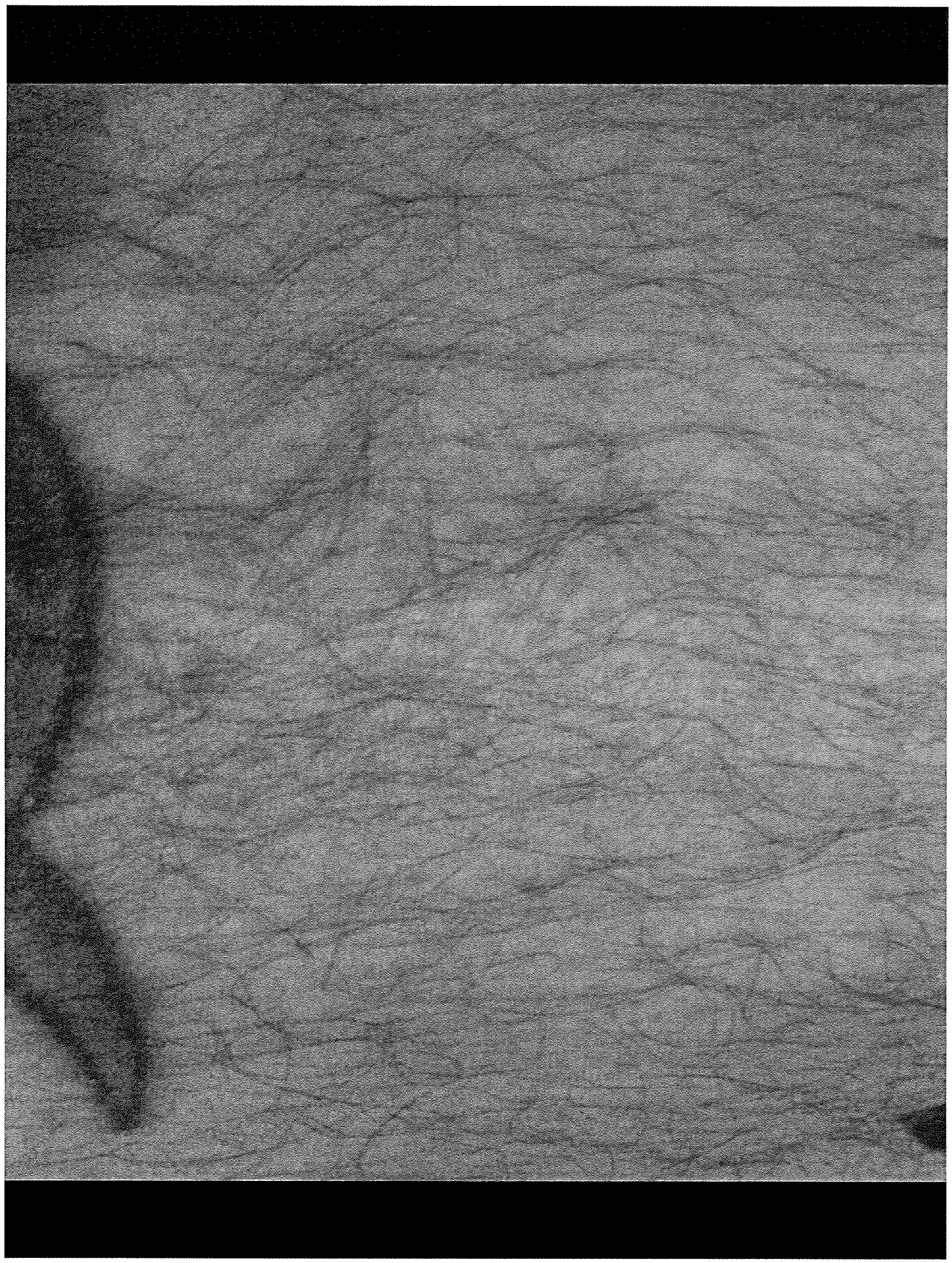
FIG. 4 shows the FIG. 1 leg burn, without scarring, twenty-five days after an anti-burn cream of the present invention was applied.

Hot coffee was accidently spilled on the skin of a subject which caused a red, second degree burn as shown in FIG. 1. On the day after the burn, an anti-burn cream of the present invention including silver sulfadiazine, lidocaine and diphenhydramine was applied to the burned skin area. No further cream applications were made to the burned skin area. FIG. 2 shows the burned skin area seven days after the burn, FIG. 3 shows the burned skin area fourteen days after the burn and FIG. 4 shows the burned skin area, without scarring, 25 days after the burn.

Example 2: Treatment of a Cut with Anti-Bruise Cream

Figure 5:
FIG. 5 shows a cut on a subject's leg before application of anti-bruise cream of the present invention.
Figure 6:
FIG. 6 shows the cut on the FIG. 5 subject's leg after application of anti-bruise cream of the present invention.

As shown in FIG. 5, a subject suffered a bleeding cut above the knee about two inches in length. Anti-bruise cream of the present invention having a vasoconstrictor was topically applied to the cut. As shown in FIG. 16, there was no further blood coming out of the cut 17 minutes after application of the anti-bruise cream.

Example 3: Application of Anti-Bruise Cream to Face Following Dermal Filler Injection After dermal filler was injected into a subject's face, anti-bruise cream of the present invention was applied to the site of the injection. Active bleeding at the injection site quickly stopped after application of the anti-bruise cream and, using a chromometer, an 80% reduction in bruising was observed as compared with similar injections where a bruise cream of the present invention was not applied. Once the bruise cream of the present invention dries, it serves as a barrier.

In the foregoing specification, the invention has been described with reference to specific preferred embodiments and methods. It will, however, be evident to those of skill in the art that various modifications and changes may be made without departing from the broader spirit and scope of the invention as set forth in the amended claims. For example, while the topical medications of the present invention have been described in connection with treating skin damage, topical medications of the present application also have ophthalmologic uses. Moreover, the bruise cream of the present invention can be used inside the body to help control bleeding as an alternative to expensive thrombin which, as a protein, can cause an allergic reaction. The specification and figures are, accordingly, to be regarded in an illustrative, rather than restrictive sense; the invention being limited only by the appended claims.

What is claimed is:
1. A topical skin healing medication comprising therapeutically effective amounts of silver sulfadiazine; diphenhydramine; lidocaine; and a petrolatum-based compounding agent.

* * * * *